US010449164B2

(12) United States Patent
Günther et al.

(10) Patent No.: US 10,449,164 B2
(45) Date of Patent: Oct. 22, 2019

(54) METHODS OF TREATING OCULAR DISORDERS USING SEMIFLUORINATED ALKANES

(71) Applicant: Novaliq GmbH, Heidelberg (DE)

(72) Inventors: Bernhard Günther, Dossenheim (DE); Bastian Theisinger, Mannheim (DE); Sonja Theisinger, Mannheim (DE); Dieter Scherer, Laufen (CH)

(73) Assignee: NOVALIQ GMBH, Heidelberg (DE)

( * ) Notice: Subject to any disclaimer, the term of this patent is extended or adjusted under 35 U.S.C. 154(b) by 255 days.

(21) Appl. No.: 14/427,927

(22) PCT Filed: Sep. 12, 2013

(86) PCT No.: PCT/EP2013/068882
§ 371 (c)(1),
(2) Date: Mar. 12, 2015

(87) PCT Pub. No.: WO2014/041055
PCT Pub. Date: Mar. 20, 2014

(65) Prior Publication Data
US 2015/0224064 A1   Aug. 13, 2015

(30) Foreign Application Priority Data

Sep. 12, 2012 (EP) .................................... 12183997

(51) Int. Cl.
| *A61K 31/02* | (2006.01) |
| *A61K 9/48*  | (2006.01) |
| *A61K 47/06* | (2006.01) |
| *A61K 9/00*  | (2006.01) |

(52) U.S. Cl.
CPC ............ *A61K 31/02* (2013.01); *A61K 9/0048* (2013.01); *A61K 47/06* (2013.01)

(58) Field of Classification Search
CPC ....... A61K 31/02; A61K 47/06; A61K 9/0048
See application file for complete search history.

(56) References Cited

U.S. PATENT DOCUMENTS

| 2,616,927 | A  | 11/1952 | Kauck et al. |
| 5,077,036 | A  | 12/1991 | Long |
| 5,326,566 | A  | 7/1994  | Parab |
| 5,336,175 | A  | 8/1994  | Mames |
| 5,518,731 | A  | 5/1996  | Meadows |
| 5,667,809 | A  | 9/1997  | Trevino et al. |
| 5,874,469 | A  | 2/1999  | Maniar et al. |
| 5,874,481 | A  | 2/1999  | Weers et al. |
| 5,980,936 | A  | 11/1999 | Krafft et al. |
| 5,981,607 | A  | 11/1999 | Ding et al. |
| 6,042,845 | A  | 3/2000  | Sun et al. |
| 6,113,919 | A  | 9/2000  | Reiss et al. |
| 6,159,977 | A  | 12/2000 | Reeves |
| 6,177,477 | B1 | 1/2001  | George et al. |
| 6,197,323 | B1 | 3/2001  | Georgieff |
| 6,224,887 | B1 | 5/2001  | Samour et al. |
| 6,262,126 | B1 | 7/2001  | Meinert |
| 6,294,563 | B1 | 9/2001  | Garst |
| 6,372,243 | B2 | 4/2002  | Kobuch |
| 6,391,879 | B1 | 5/2002  | Reeves |
| 6,458,376 | B1 | 10/2002 | Meadows |
| 6,486,212 | B2 | 11/2002 | Meinert |
| 6,489,367 | B1 | 12/2002 | Meinert |
| 6,730,328 | B2 | 5/2004  | Maskiewicz et al. |
| 7,001,607 | B1 | 2/2006  | Menz et al. |
| 7,258,869 | B1 | 8/2007  | Berry et al. |
| 7,740,875 | B2 | 6/2010  | Dechow |
| 8,029,977 | B2 | 10/2011 | Meinert et al. |
| 8,470,873 | B2 | 6/2013  | Chen |
| 8,614,178 | B2 | 12/2013 | Theisinger et al. |
| 8,916,157 | B2 | 12/2014 | Krause et al. |
| 8,986,738 | B2 | 3/2015  | Meinert |
| 9,241,900 | B2 | 1/2016  | Wilson |
| 9,308,262 | B2 | 4/2016  | Günther et al. |
| 9,770,508 | B2 | 9/2017  | Günther et al. |
| 10,045,996 | B2 | 8/2018 | Theisinger et al. |
| 2002/0004063 | A1 | 1/2002 | Zhang |
| 2002/0128527 | A1 | 9/2002 | Meinert |
| 2003/0018044 | A1 | 1/2003 | Peyman |
| 2003/0027833 | A1 | 2/2003 | Cleary et al. |
| 2003/0170194 | A1 | 9/2003 | Piotroviak |
| 2004/0265362 | A1 | 12/2004 | Susilo |

(Continued)

FOREIGN PATENT DOCUMENTS

| EP | 0 670 159 A1 | 9/1995 |
| EP | 0 939 655 B1 | 6/2002 |

(Continued)

OTHER PUBLICATIONS

Blackie et al. "MGD: Getting to the Root Cause of Dry Eye Eye" Review of Optometry, Jun. 21, 2012, pp. 1-12.*
Troiano et al. "Effect of Hypotonic ).4% Hyaluronic Acid Drops in Dry Eye Patients: A Cross-Over Study", Clinical Science, 2008, vol. 27, issue 10, pp. 1126-1130, abstract provided.*
WebMD: Hyaluronic acid (http://www.webmd.com/vitamins-supplements/ingredientmono-1062-hyaluronic%20acid.aspx?activeingredientid=1062&) printed Mar. 23, 2017, pp. 1-2.*
Troiano et al. "Effect of Hypotonic 0.4% Hyaluronic Acid Drops in Dry Eye Patients: A Cross-Over Study", Cornea, 2008, vol. 27, pp. 1126-1130.*

(Continued)

*Primary Examiner* — Kendra D Carter
(74) *Attorney, Agent, or Firm* — Hoxie & Associated LLC (57) ABSTRACT

The invention provides novel compositions comprising at least two or more semifluorinated alkanes. The compositions can be used as medicines that are topically administered to an eye or ophthalmic tissue, such as for use in the treatment of keratoconjunctivitis sicca (dry eye) and/or meibomian gland dysfunction and symptoms associated therewith. The invention further provides kits comprising such compositions.

11 Claims, 1 Drawing Sheet

(56) References Cited

U.S. PATENT DOCUMENTS

| | | |
|---|---|---|
| 2004/0266702 A1 | 12/2004 | Dawson et al. |
| 2005/0079210 A1 | 4/2005 | Gupta |
| 2005/0175541 A1 | 8/2005 | Lanza et al. |
| 2005/0288196 A1 | 12/2005 | Horn |
| 2006/0153905 A1 | 7/2006 | Carrara et al. |
| 2008/0153909 A1 | 6/2008 | Dana et al. |
| 2008/0207537 A1 | 8/2008 | Turner et al. |
| 2008/0260656 A1 | 10/2008 | Mallard |
| 2010/0008996 A1 | 1/2010 | Meinert |
| 2010/0226997 A1 | 9/2010 | Bowman et al. |
| 2010/0274215 A1 | 10/2010 | Wong et al. |
| 2011/0269704 A1 | 11/2011 | Seigfried |
| 2012/0010280 A1 | 1/2012 | Aleo et al. |
| 2012/0095097 A1 | 4/2012 | Tabuchi et al. |
| 2012/0238639 A1 | 9/2012 | Theisinger et al. |
| 2013/0046014 A1 | 2/2013 | Theisinger et al. |
| 2013/0084250 A1 | 4/2013 | Hagedorn et al. |
| 2013/0266652 A1 | 10/2013 | Theisinger et al. |
| 2013/0303473 A1 | 11/2013 | Wilson |
| 2014/0004197 A1 | 1/2014 | Theisinger et al. |
| 2014/0100180 A1 | 4/2014 | Gunther et al. |
| 2014/0140942 A1 | 5/2014 | Gunther et al. |
| 2014/0369993 A1 | 12/2014 | Gunther et al. |
| 2015/0238605 A1 | 8/2015 | Günther et al. |
| 2016/0101178 A1 | 4/2016 | Wilson |
| 2016/0159902 A1 | 6/2016 | Günther et al. |
| 2017/0087100 A1 | 3/2017 | Scherer et al. |
| 2017/0087101 A1 | 3/2017 | Scherer et al. |
| 2017/0182060 A1 | 6/2017 | Wiedersberg et al. |

FOREIGN PATENT DOCUMENTS

| | | |
|---|---|---|
| EP | 1 152 749 B1 | 4/2006 |
| EP | 2 332 525 A1 | 6/2011 |
| EP | 2 335 735 A1 | 6/2011 |
| EP | 2 462 921 A1 | 6/2012 |
| JP | S6452722 | 2/1989 |
| JP | 2000511157 | 8/2000 |
| JP | 2001/158734 | 6/2001 |
| JP | 2008/505177 | 2/2008 |
| JP | 2011/006348 | 1/2011 |
| WO | WO 1995/033447 | 12/1995 |
| WO | WO 96/40052 A1 | 12/1996 |
| WO | WO 97/12852 A1 | 4/1997 |
| WO | WO 1998/005301 | 12/1998 |
| WO | WO 00/24376 A1 | 5/2000 |
| WO | WO 00/54588 A1 | 9/2000 |
| WO | WO 2002/49631 | 6/2002 |
| WO | WO 2005/099718 A1 | 10/2005 |
| WO | WO 2005/099752 | 10/2005 |
| WO | WO 2005/123035 A1 | 12/2005 |
| WO | WO 2006/007510 A1 | 1/2006 |
| WO | WO 2006/042059 | 4/2006 |
| WO | WO 2006/048242 | 5/2006 |
| WO | WO 2007/052288 A2 | 5/2007 |
| WO | WO 2008/060359 A2 | 5/2008 |
| WO | WO 2010/062394 A2 | 6/2010 |
| WO | WO 2010/146536 | 12/2010 |
| WO | WO 2011/009436 | 1/2011 |
| WO | WO 2011/073134 A1 | 6/2011 |
| WO | WO 2011/113855 | 9/2011 |
| WO | WO 2012/052418 A1 | 4/2012 |
| WO | WO 2012/062834 A1 | 5/2012 |
| WO | WO 2012/093113 A1 | 7/2012 |
| WO | WO 2012/121754 | 9/2012 |
| WO | WO 2012/160179 A2 | 11/2012 |
| WO | WO 2012/160180 A2 | 11/2012 |
| WO | WO 2013/110621 A1 | 8/2013 |
| WO | WO 2014/041055 | 3/2014 |
| WO | WO 2014/041071 A1 | 3/2014 |
| WO | WO 2014/154531 | 10/2014 |
| WO | WO 2015/011199 | 1/2015 |

OTHER PUBLICATIONS

Ahmed, I. et al., "Disposition of Timolol and Inulin in the Rabbit Eye Following Corneal Versus Non-Corneal Absorption," International Journal of Pharmaceutics, 1987, 38, 9-21.

Baerdemaeker, L. et al., "Pharmacokinetics in Obese Patients," Continuing Education in Anaesthesia, Critical Care & Pain, 2004, 4, 152-155.

Broniatowski, M. et al., "Langmuir Monolayers Characteristic of (Perfluorodecyl)-Alkanes," Journal of Physical Chemistry B, 2004, 108, 13403-13411.

Chemical Book, 5-Fluorouracil, available at <http://www.chemicalbook.com/ChemicalProductProperty_EN_CB8162744.htm>, accessed Mar. 7, 2014, 1 page.

Davies, N., "Biopharmaceutical Considerations in Topical Ocular Drug Delivery," Clinical and Experimental Pharmacology and Physiology, 2000, 27, 558-562.

Dembinski, R. et al., "Semi-fluorinated Alkanes as Carriers for Drug Targeting in Acute Respiratory Failure," Experimental Lung Research, 2010, 36, 499-507.

Elkeeb, R. et al., "Transungual Drug Delivery: Current Status," International Journal of Pharmaceutics, 2010, 384, 1-8.

English-language machine translation of EP0670159 (A1) issued in U.S. Appl. No. 14/122,025 on Apr. 1, 2015, 10 pages.

Freiburger Dokumentenserver (FreiDok), Albert-Ludwigs-Unversitaät Freiburg, retrieved from http://www.freidok.uni-freiburg.de/volltexte/5682/, retrieved on Feb. 5, 2014, 2 pages.

Gayton, J., "Etiology, Prevalence, and Treatment of Dry Eye Disease," Clinical Ophthalmology, 2009, 3, 405-412.

Griffin, W., "Classification of Surface-Active Agents by 'HLB'," Journal of the Society of Cosmetic Chemists, 1949, 1, 311-326.

Hoerauf, H. et al., "Combined Use of Partially Fluorinated Alkanes, Perfluorocarbon Liquids and Silicone Oil: An Experimental Study," Graefe's Archive for Clinical and Experimental Ophthalmology, 2001, 239 (5), 373-381.

International Preliminary Report on Patentability for International Application No. PCT/EP2011/068141 dated Apr. 23, 2013, 4 pages.

International Preliminary Report on Patentability for International Application No. PCT/EP2011/069795 dated May 14, 2013, 8 pages.

International Preliminary Report on Patentability for International Application No. PCT/EP2012/050043 dated Jul. 10, 2013, 5 pages.

International Preliminary Report on Patentability for International Application No. PCT/EP2012/059787 dated Nov. 26, 2013, 9 pages.

International Preliminary Report on Patentability for International Application No. PCT/EP2012/059788 dated Nov. 26, 2013, 8 pages.

International Preliminary Report on Patentability for International Application No. PCT/EP2013/051163 dated Jul. 29, 2014, 7 pages.

International Preliminary Report on Patentability for International Application No. PCT/EP2013/068882 dated Mar. 17, 2015, 5 pages.

International Preliminary Report on Patentability for International Application No. PCT/EP2013/068909 dated Mar. 17, 2015, 7 pages.

International Search Report for International Application No. PCT/EP2011/068141 dated Dec. 14, 2011, 2 pages.

International Search Report for International Application No. PCT/EP2011/069795 dated Jan. 16, 2012, 3 pages.

International Search Report for International Application No. PCT/EP2012/050043 dated Apr. 24, 2012, 2 pages.

International Search Report for International Application No. PCT/EP2012/059787 dated Dec. 5, 2012, 4 pages.

International Search Report for International Application No. PCT/EP2012/059788 dated Dec. 3, 2012, 4 pages.

International Search Report for International Application No. PCT/EP2013/051163 dated Mar. 4, 2013, 4 pages.

International Search Report for International Application No. PCT/EP2013/068882 dated Oct. 30, 2013, 4 pages.

International Search Report for International Application No. PCT/EP2013/068909 dated Dec. 5, 2013, 4 pages.

Knepp, V. et al., "Stability of Nonaqueous Suspension Formulations of Plasma Derived Factor IX and Recombinant Human Alpha Interferon at Elevated Temperatures," Pharmaceutical Research, 1998, 15 (7), 1090-1095.

(56) References Cited

OTHER PUBLICATIONS

Kociok, N., et al, "Influence on Membrane-Mediated Cell Activation by Vesicles of Silicone Oil or Perfluorohexyloctane," Graefe's Archive for Clinical and Experimental Ophthalmology, 2005, 243, 345-358.

Lemp, M., "Management of Dry Eye Disease," The American Journal of Managed Care, 2008, 14 (3), S88-S101.

Mackiewicz, J. et al., "In Vivo Retinal Tolerance of Various Heavy Silicone Oils," Investigative Ophthalmology & Visual Science, 2007, 48 (4), 1873-1883.

Meinert, H. et al., "The Use of Semifluorinated Alkanes in Blood-Substitutes," Biomaterials, Artificial Cells, and Immobilization Biotechnology, 1993, 21 (5), 583-595.

Meinert, H. et al., "Semifluorinated Alkanes—A New Class of Compounds with Outstanding Properties for Use in Ophthalmology," European Journal of Ophthalmology, 2000, 10 (3), 189-197.

Murdan, S., "Enhancing the Nail Permeability of Topically Applied Drugs," Expert Opinion on Drug Delivery, 2008, 5 (11), 1267-1282.

Perry, H., "Dry Eye Disease: Pathophysiology, Classification, and Diagnosis," The American Journal of Managed Care, 2008, 14 (3), S79-S87.

Pinarci, E. et al., "Intraocular Gas Application in the Diagnosis and Treatment of Valsalva Retiopathy in Case with Premacular Hemorrhage," XP002625604, Retina-Vitreus, 2009, 17 (2), 153-155, abstract only.

Plassmann, M. et al., "Trace Analytical Methods for Semifluorinated n-Alkanes in Snow, Soil, and Air," Analytical Chemistry, 2010, 82(11), 4551-4557.

Plassmann, M. et al., "Theoretical and Experimental Simulation of the Fate of Semifluorinated n-Alkanes During Snowmelt," Environmental Science & Technology, 2010, 44 (17), 6692-6697.

Rosca-Casian, O. et al., "Antifungal Activity of Aloe vera Leaves," Fitoterapia, 2007, 28, 219-222.

Rosenberg, A., "Effects of Protein Aggregates: An Immunologic Perspective," The AAPS Journal, 2006, 8 (3), E501-E507.

Stevenson, C., "Characterization of Protein and Peptide Stability and Solubility in Non-Aqueous Solvents," Current Pharmaceutical Biotechnology, 2000, 1, 165-182.

Wang, W., "Lyophilization and Development of Solid Protein Pharmaceuticals," International Journal of Pharmaceutics, 2000, 203, 1-60.

Wong, D. et al., "Perfluorocarbons and Semifluorinated Alkanes," Seminars in Ophthalmology, 2000, 15 (1), 25-35.

Gerdenitsch, "Emulsions—established and promising drug carriers for parenteral adminstration", retrieved from internet: http://ipimediaworld.com/wp-content/uploads/2012/05/Pages-from-IPI-Volume-2-Issue-1-11.pdf. Retrieved on May 23, 2016.

JP 2000511157A, English Machine Translation of the Abstract, Description, and Claims, Espacenet, Date Accessed: Feb. 10, 2016.

JPS6452722, English Machine Translation of the Abstract, Description, and Claims, Espacenet, Date Accessed: Feb. 10, 2016.

Kaercher et al., "NovaTears® as new Therapy in Dry Eye Results from three prospective, multicenter, non-interventional studies in different patient populations", TFOS Conference (Tear Film & Ocular Surface), Sep. 7-10, 2016, Montpellier, France, Poster Session II, Poster No. 60, 1 page.

Messmer, et al. "Semifluorierte Alkane als Therapie bei Meibomdrüsen-Dysfunktion Ergebnisse einer prospektiven, multizentrischen Beobachtungsstudie", Presentation, DOG-Kongress, Sep. 29-Oct. 2, 2016, Berlin DOG (Deutsche Ophtalmologische Gesellschaft), Poster No. PSa03-02, 1 page (German language version).

Messmer, et al. "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Poster No. PSa03-02, English Translation, 6 pages.

Messmer, et al. "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Ophthalmologe, Aug. 2016 Poster No. PSa03-02, English Translation of Abstract, p. 138.

Schnetler et al., "Lipid composition of human meibum: a review", S Afr Optom, 2013, 72(2):86-93.

Spöler et al., ""Towards a New in vitro Model of Dry Eye: The ex vivo Eye Irritation Test"", Developments in Ophthalmology, 2010, 45:93-107.

Tiffany, J.M., "Individual Variations in Human Meibomian Composition", Exp. Eye Res., 1978, 27:289-300.

Chhadva et al., "Meibomian Gland Disease the Role of Gland Dysfunction in Drye Eye Disease," Ophthalmology (2017) 124(11 Supplement): S20-S26.

Costa Gomes et al., "Solubility of dioxygen in seven fluorinated liquids," Journal of Fluorine Chemistry, 2004, 125, 1325-1329.

Dias et al., "Solubility of oxygen in liquid perfluorocarbons," Fluid Phase Equilibria, 2004, 222-223:325-330.

Gehlsen et al., "A semifluorinated alkane (F4H5) as novel carrier for cyclosporine A: a promising therapeutic and prophylactic option for topical treatment of dry eye," Graefe's Arch. Clin. Exp. Ophthalmol., (2017) 255(4):767-775.

Gehlsen. U., et al., "Cyclosporine A using F4H5 as liquid drug carrier is effective in treating experimental dry-eye disease," Investigative Ophthalmology & Visual Science, 2015, 56(319), Abstract Only (2 pages).

Hardung, H., "Semifluorierte und perfluorierte Verbindungen zur topischen und parenteralen Anwendung," 2008, retrieved from http://www.freidok.uni-freiburg.de/volltexte/5682/pdf/Dissertation_Hardung.pdf (retrieved on Oct. 10, 2011).

Hardung, H., "Semifluoriete und perfluorierte Verbindungen zur topischen und parenteralen Anwendung," 2008, English Language Abstract, 2 pages, retrieved from https://freidok.uni-freiburg.de/data/5682 (retrieved on Jul. 10, 2017).

Holm, R. et al., "A novel excipient, 1-perfluorohexyloctane shows limited utility for the oral delivery of poorly water-soluble drugs," European Journal of Pharmaceutical Sciences, 2011, 42: 416-422.

Ishizaki et al., "Treatment of Diabetic Retinopathy", Forum: Complication, Practice, 2009, 26(5): 474-476 (3 pages).

Lin, H. et al., "Dry eye disease: A review of diagnostic approaches and treatments," Saudi Journal of Ophthalmology, 2014, 28:173-181.

Messmer, E.M., "The Pathophysiology, Diagnosis, and Treatment of Dry Eye Disease," (2015) Deutsches Arzteblatt International, 112(5):71-82.

O'Ourke, M. et al., "Enhancing Delivery of Topical Ocular Drops," Cataract & Refractive Surgery Today Europe, 2016, 2 pages.

Pflugfelder et al., "The Pathophysiology of Dry Eye Disease What We Know and Future Directions for Research," Ophthalmology (2017) 124(11 Supplement): S4-S13.

Sall, K. et al. "Two Multicenter, Randomized Studies of the Efficacy and Safety of Cyclosporine Ophthalmic Emulsion in Moderate to Severe Dry Eye Disease," Ophthalmology, 2000, 107(4):631-639.

Steven, P. et al. "Semifluorinated Alkane Eye Drops for Treatment of Dry Eye Disease—A Prospective, Multicenter Noninterventional Study" Journal of Ocular Pharmacology and Therapeutics (2015) vol. 31(8):498-503.

Steven et al., "Semifluorinated Alkane Eye Drops for Treatment of Dry Eye Disease Due to Meibomian Gland Disease," Journal of Ocular Pharmacology and Therapeutics, 2017, 33(9):1-8.

"What is retinal vitrectomy?", Presented by: Medical Online, Obesity and Diabetes Mellitus, 2005, 4(2): 284-286 (3 pages).

Bardin et al., "Long-Range Nanometer-Scale Organization of Semifluorinated Alkane Monolayers at the Air/Water Interface," Langmuir, 2011, 27:13497-13505.

Zhang et al., "Surface micelles of semifluorinated alkanes in Langmuir-Blodgett monolayers," Phys. Chem. Chem. Phys., 2004, 6:1566-1569.

\* cited by examiner

METHODS OF TREATING OCULAR DISORDERS USING SEMIFLUORINATED ALKANES

CROSS REFERENCE TO RELATED APPLICATIONS

This application is the National Stage Entry under 35 U.S.C. § 371 of International Application No. PCT/EP2013/068882 filed Sep. 12, 2013, which claims priority to European Patent Application No. 12183997.1 filed Sep. 12, 2012, the contents of each of which are incorporated herein by reference.

FIELD

The present invention is in the field of ophthalmic compositions, in particular topical ophthalmic compositions which are useful in the treatment keratoconjunctivitis sicca and/or meibomian gland dysfunction and symptoms associated therewith.

BACKGROUND

Keratoconjunctivitis sicca, also known as dry eye disease, or dysfunctional tear syndrome, is a multifunctional disorder of the tear film, and ocular surface which results in discomfort, visual disturbance, and often even in ocular surface damage. Its prevalence differs widely by regions and is estimated to range from about 7.4% in the USA to about 33% in Japan (J. L. Gayton, Clinical Ophthalmology 2009:3, 405-412). According to another estimate, approximately 3.2 million women and 1.05 million men suffer from keratoconjunctivitis sicca in the USA alone. If symptomatically mild cases are also considered, there could be as many as 20 million affected people in the USA.

The main physiological function of the tear film is the lubrication of the ocular surface and the inner eyelid. In addition, it supplies the ocular surface with the nutrients which it requires, provides a smooth and regular optical surface for the eye. Moreover, it protects the ocular surface against pathogens by various mechanisms, including mechanical removal of foreign particles but also through antimicrobial substances which it contains. Consequently, the loss in dynamic stability of the structure, composition, volume and distribution, as well as clearance of the tear film can lead to the development of dry eye disease.

The tear film is a dynamic structure composed of a mucous component, an aqueous component, and a lipid component. The innermost layer of the film is the mucous layer or component, which is bound to the ocular epithelium via the interaction of mucin molecules which are produced by conjunctival goblet cells and by stratified squamous cells of the conjunctiva and the cornea. The lubricating effect of the tear film is substantially based on the mucous layer and its composition.

On top of the mucous layer is the aqueous layer which is produced by the main and accessory lacrimal glands. Its primary function is to hydrate the mucous component and contribute to the transport of nutrients, electrolytes, antibacterial compounds, and oxygen to the ocular surface. The aqueous component contains water, electrolytes, lysozyme, lactoferrin, immunoglobulins (in particular IgA), retinol, hepatocyte growth factor, epidermal growth factor as its important constituents.

The outermost layer is the lipid layer, covering the aqueous layer. The lipid layer is formed from meibum (a complex mixture of polar and non-polar lipids including wax and cholesterol esters, phospholipids, di- and tri-glycerides and hydrocarbons) secreted by the meibomian (tarsal) glands which are positioned at the tarsal plates of the eyelids, and to some degree also by the glands of Zeis which open into the eyelash follicles. The lipid mixture, which has a low melting point and remains fluid at tissue and corneal temperature, is secreted into the marginal reservoirs of the upper and lower eyelid margins. It is understood that the blinking action helps to promote the spreading and mixing of the lipids in the lipid layer. The major role of the lipid layer is primarily to reduce the rate of evaporation of the aqueous layer by evaporation, but its functions also include enhancing the spreading of the tear film, forming a barrier to prevent tear film contamination, and providing a clear optical surface. It has been proposed that increased tear film stability is associated with a thicker tear film lipid layer.

It is today acknowledged that keratoconjunctivitis sicca is a complex, multifunctional disorder involving several interacting pathophysiological mechanisms which are only beginning to be understood (H. D. Perry, Am. J. Man. Care 13:3, S79-S87, 2008). The two mechanisms that are being discussed as pivotal in the etiology of this disease and which also appear to reinforce each other mutually are tear hyperosmolarity and tear film instability. Hyperosmolar tear fluid can result from excessive tear film evaporation or reduced aqueous flow. It activates an inflammatory cascade and causes the release of inflammatory mediators into the tear fluid, with multiple pathophysiological effects eventually leading to further increased tear film evaporation and tear film instability. Thus, tear film instability can be a consequence of hyperosmolarity. Alternatively, tear film instability can also develop through its own etiological pathway, for example via abnormalities of the lipid layer composition, such as from meibomian gland disease.

The inflammation cycle is one of the key processes that maintain and potentially progress the dry eye disease. Depending on the severity of the condition, patients often develop a reversible squameous metaphase and punctate erosions of the ocular epithelium. Secondary diseases whose development may be triggered by dry eye disease include filamentary keratitis, microbial keratitis, corneal neovascularisation, and ocular surface keratinisation.

Two major categories of dry eye disease (DED) are distinguished today, which are aqueous-deficient DED and evaporative DED. These conditions are not necessarily mutually exclusive.

Within the class of aqueous-deficient forms of DED, two major subtypes are differentiated, Sjögren and non-Sjögren. Sjögren syndrome patients suffer from autoimmune disorders in which the lacrimal glands are invaded by activated T-cells, which leads not only to keratoconjunctivitis sicca but also to a dry mouth condition. The Sjögren syndrome can be a primary disease or result from other autoimmune diseases such as systemic lupus erythrematosus or rheumathroid arthritis. Non-Sjögren patients suffering from an aqueous-deficient DED usually have a lacrimal gland insufficiency, lacrimal duct obstruction or reflex hyposecretion.

The second major class, evaporative DED, is also somewhat heterogeneous and can develop as a result of diverse root causes. Causes associated with increased evaporative loss of the tear film include meibomian gland disease, eyelid aperture disorders, blink disorders (as in Parkinson disease) or ocular surface disorders (as in allergic conjunctivitis). In particular, meibomian gland diseases are prevalently associated with evaporative dry eye disease. For example, meibomian gland dysfunction can result in changes in the quantitative or qualitative secretion of the lipid components required for the tear film. This in turn can lead to a failure in forming a stable and continuous tear film, which is followed by evaporative loss and hyperosmolarity. Meibomian gland dysfunction can often be characterized by gland obstruction and clogging through hyperkeratinisation of the gland and increased viscosity of the meibum. Dysfunction can arise from a primary lid-margin related disease or a secondary disease arising from systemic disorders such as acne rosacea or seborrheic dermatitis.

Among the many risk factors for dry eye disease that are known today, some of the best studied ones are advanced age and female sex. It appears that in particular postmenopausal women have a reduced tear production, probably related to hormonal effects which are not very well understood as yet. Further risk factors include diets with low omega-3-fatty acids, occupational factors (e.g. associated with reduced blink frequency), environmental conditions, contact lens wearing, ophthalmic surgery, certain systemic (anticholinergics, beta-blockers, isotretinoin, interferons, hormones) and ophthalmic medications (any frequently administered eye drops including artificial tears; especially formulations comprising preservatives), and a number of primary diseases such as Parkinson disease, hepatitis C, HIV infection, and diabetes mellitus.

The management of dry eye disease relies on both non-pharmacological and pharmacological approaches and the therapeutic options depend significantly on the severity of the disease state (M. A. Lemp, Am. J. Man. Care 14:3, S88-S101, 2008).

Pharmacological treatments are required for moderate to more severe forms of keratoconjunctivitis sicca. However, there are presently not many pharmacological therapies available which have proven to be effective and/or which have been authorized by the regulatory agencies. Treatment options with pharmaceutical active ingredients such as secretagogues (e.g. cholinergic agents such as muscarinic acetylcholine receptor antagonists) to stimulate tear production, and anti-inflammatory agents such as corticosteroids and oral tetracyclines have been proposed. In the US, the major pharmacological treatment for moderate to severe keratoconjunctivitis sicca is with ciclosporin (i.e. ciclosporin A, also known as cyclosporine A), which is an approved medicine in the form of an ophthalmic emulsions (Restasis®) for increasing ". . . tear production in patients whose tear production is presumed to be suppressed due to ocular inflammation associated with keratoconjunctivitis sicca." (Restasis prescribing information). In this case, according to the evidence that is available, topical ciclosporin is probably disease-modifying rather than only palliative.

Non-pharmacological approaches to treating dry eye disease and its symptoms are used initially when only mild symptoms occur, but also as palliative measures to support pharmacological and medical interventions. Non-pharmacological approaches may include the avoidance of exacerbating factors such as dry air, wind and drafts, tobacco smoke, modification of working habits; eye lid hygiene; tear supplementation; physical tear retention by punctal plugs or therapeutic contact lenses. In the case of dry eye disease exacerbated or caused by meibomian gland dysfunction, measures such as heat compresses, eye lid massaging or forced expression of the glands are also often recommended.

The mainstay of non-pharmacological DED treatment is the use of artificial tears for tear substitution. Most of the available products are designed as lubricants. In addition, they may function as carriers for nutrients and electrolytes (importantly, potassium and bicarbonate), and some products attempt to correct physical parameters such as an increased osmolarity in certain forms of DED. The major functional component of artificial tear compositions is an agent which increases or adjusts the viscosity, so as to increase retention time on the ocular surface and which at the same time also exhibits lubricant functionality. Common compounds used for this purpose include carboxymethylcellulose and its sodium salt (CMC, carmellose), polyvinyl alcohol, hydroxypropyl methylcellulose (HPMC, hypromellose), hyaluronic acid and its sodium salt, and hydroxypropyl guar gum. Hydrocolloids such as hydroxypropyl guar gum or hyaluronic acid exhibit some degree of bioadhesiveness and can act to add volume to the tear film. However, compositions with a relatively high viscosity, and in particular gel-type formulations, may have a tendency to cause visual blurring, as well as a tendency to cake and form residues on the eye margins and eyelashes.

Some artificial tears comprise lipids as substitutes for the lipid component, with the intention of mimicking the lipid layer of the natural tear film in order to decrease the rate of tear fluid evaporation. For example, U.S. Pat. No. 5,981,607 discloses compositions for the alleviation of symptoms related to dry eye based emulsions with higher fatty glycerides such as castor oil, corn oil or sunflower oil or light mineral oil. These types of lipids are, however physically and biochemically poorly related to native lipid compositions. Also, the exact fate of an emulsion mixed with tear fluid in a physiological setting is not completely predictable, especially in view of the variability in volume and content of the tear film in patients with dry eye disease.

In general, one of the disadvantages of such formulations comprising oil for ophthalmic administration is that these inherently may have a negative impact on vision. Whether used as oily solutions or oil-in-water emulsions, they exhibit a refractive index which differs substantially from that of physiological tear fluid, which leads to visual disturbances and blurring.

Also, in contrast to single phase systems, emulsions may be more complex and difficult to manufacture, especially in sterile form. Frequently, emulsions are not readily sterilisable by thermal treatment without negative impact on the physical properties of the emulsion. On the other hand, aseptic processing is complex, costly, and is associated with higher risks of failure, i.e. microbial contamination.

Oil-in-water emulsions are also more prone to microbial contamination during use as well. If they were to be presented in multi-dose containers which are in principle more cost-efficient and convenient for patients than single-use vials, they would have to be preserved in order to ensure their microbiological quality.

At the same time however, preservatives which can be used in ophthalmic formulations are potentially damaging to the eye, in particular to the ocular surface, and should be avoided in the context of dry eye disease. At least in earlier years, multi-dose formulations for ophthalmic administration had to be preserved using a physiologically acceptable preservative in order to reduce the risk of microbial contamination and infection. Most preservatives are however problematic for DED patients in that they have a potential to negatively affect the ocular surface, thus counteracting the therapeutic intent. This is particularly relevant for patients with moderate to severe dry eye disease symptoms who may require frequent use for symptom relief, as well as patients who require multiple preserved topical medicaments.

As an alternative, single-dose containers for the administration of non-preserved formulations were developed.

These are however less cost-efficient and convenient to handle for the patient than the conventional multi-dose bottle. Furthermore, ophthalmic formulations utilizing 'vanishing' preservatives such as sodium chlorite or sodium perborate, which can convert to non-toxic ions and water after instillation and contact with the tear film, may still be irritating to patients especially those with severe disease who may not have sufficient tear volume to effectively degrade the preservatives.

WO 2011/073134 discloses ophthalmic topical pharmaceutical compositions comprising immunosuppressant macrolides such as ciclosporin A and semifluorinated alkanes, for treatment of keratoconjunctivitis sicca. The semifluorinated alkanes in the disclosed compositions serve as suitable liquid vehicles for delivering the therapeutic pharmaceutical agent to the eye, and in particular have a high capacity for dissolving extremely challenging poorly soluble compounds such as ciclosporin. However, no mention has been made as to the protective effect and spreading behaviour, in particular of synergistic semifluorinated alkane mixtures, on the tear film and the tear film lipid layer. Nor does the document discuss the solubilizing effect semifluorinated alkane mixtures may have for altered state meibum (such as the case in meibomian gland dysfunction, in which glands may be clogged).

U.S. Pat. No. 7,001,607 discloses a polyaphron gel tear substitute containing at least one water-soluble fluorinated surfactant, water, and a non-polar component, in which the nonpolar component can be fluorocarbon or a silicone oil. The gel compositions are specifically administered into the conjunctival sac to form a gel reservoir, and are only spread over the cornea of the eye as a liquid film over the cornea as a result of blinking action. For patients with dry eye symptoms caused by eyelid/blink disorders (e.g. as a result of Parkinson's disease), such compositions are therefore not useful. Moreover, as blinking is necessary to spread and liquefy the gel, it is likely that there would be significant visual blurring directly after instillation, which is also likely to be worse when incorrectly applied by the patient not directly into the conjunctival sac. Furthermore, the proposed fluorinated surfactants do not have an established clinical record of tolerability to the human eye, and they can have a damaging effect on the ocular surface (despite inclusion of non-polar components which may interact more strongly with them) once mixed with physiological tear fluid.

It is therefore an object of the present invention to provide a novel composition which is useful in the treatment of dry eye disease and symptoms and conditions associated therewith, and which at the same time addresses and overcomes the various issues and at least one of the limitations or disadvantages associated with prior art formulations. In a specific aspect, it is an object of the invention to provide a composition for the palliative treatment and care of the eye and eye tissue. In a further aspect, it is an object of the invention to provide a kit comprising a composition for the treatment of keratoconjunctivitis sicca which does not exhibit one or more of the disadvantages of prior art. Further objects of the invention will become clear on the basis of the following description, examples, and patent claims.

SUMMARY OF THE INVENTION

The present invention provides a novel composition comprising at least, but not limited to, two semifluorinated alkanes. The composition can be used as a medicine, in particularly as a medicine that is topically administered to an eye or ophthalmic tissue. Alternatively, the composition can be used as a cleansing solution for the eye or ophthalmic tissue.

In one of the preferred embodiments, the composition comprises a first semifluorinated alkane of formula $F(CF_2)_n(CH_2)_mH$, wherein n is an integer from the range of 3 to 8 and m is an integer from the range of 3 to 10 and a second semifluorinated alkane of the formula $F(CF_2)_n(CH_2)_mH$ wherein n is an integer from the range of 6 to 20 and m is an integer from the range of 10 to 20.

In another preferred embodiment, the invention provides the use of such a composition in the treatment of keratoconjunctivitis sicca (dry eye) and/or meibomian gland dysfunction, and any symptoms or conditions associated therewith.

In a further aspect, the invention provides the use of such a composition in the palliative treatment and care of an eye or ophthalmic tissue.

In yet a further aspect, the invention provides a pharmaceutical kit comprising such a composition in a container which has dispensing means adapted for topical administration of the composition to the eye or ophthalmic tissue.

DETAILED DESCRIPTION OF THE INVENTION

In a first aspect, the invention provides compositions comprising at least two semifluorinated alkanes. The compositions comprising at least two semifluorinated alkanes, in particular if selected as described below, are useful for medicines; in particular the compositions can be used as medicines for topical administration to the eye. The compositions are further characterized by their use in the treatment of keratoconjunctivitis sicca and related conditions.

While semifluorinated alkanes have been described in the art, e.g. in EP-A 2 335 735, as useful carriers for ophthalmic drugs for the topical treatment of conditions such as keratoconjunctivitis sicca, the present invention is based on the discovery that semifluorinated alkanes and their mixtures may themselves, even in the absence of a drug substance, be advantageously used in the therapy of such conditions.

Keratoconjunctivitis sicca is a complex, multifaceted disease or condition as described above. It is also known as dry eye syndrome, dry eye disease (DED), or dysfunctional tear syndrome. Aqueous-deficient DED, evaporative DED are within the scope of keratoconjunctivitis sicca and form specific subtypes thereof. Sjögren syndrome, lacrimal gland insufficiency, meibomian gland disease and meibomian gland dysfunction, and other conditions are also within the scope of keratoconjunctivitis sicca, being direct or indirect causes thereof.

Meibomian gland diseases cover a broad range of meibomian gland disorders including neoplasia and congenital disorders. Meibomian gland dysfunction, on the other hand is understood to be abnormalities of the meibomian glands which are often characterized by gland duct obstructions and/or changes (qualitative and/or quantitative) to the secretions of the glands. In general, conditions or disease states causing or leading to an abnormal, reduced or increased delivery of lipids to the tear film can give rise to keratoconjunctivitis sicca and the symptoms associated therewith.

Symptoms of keratoconjunctivitis sicca include a dry, scratchy, gritty, or sandy feeling in the eye; foreign body sensation; pain or soreness; stinging or burning; itching; increased blinking; eye fatigue; photophobia; blurry vision; redness; mucus discharge; contact lens intolerance; excessive reflex tearing. In addition to the symptoms of keratoconjunctivitis sicca as described, patients with meibomian gland dysfunction may also experience symptoms including itchiness, redness, swelling, pain or soreness, discharge accumulation or crusting specifically at the lid margins. It is understood that not all patients suffering from keratoconjunctivitis sicca exhibit all symptoms simultaneously. Hence, there is currently no uniform set of criteria for diagnosing the disease. It is also understood that patients may suffer from one or more subtypes of keratoconjunctivitis sicca, or one or more conditions or disease pathways causing keratoconjunctivitis sicca. It is however important to note that, within the scope of the present invention, any of the aspects, symptoms or pathophysiological consequences of dry eye disease may be addressed.

The key advantages of the present invention, such as a reduction of symptom severity of dry eye syndrome, for example a reduction of the gritty or sandy feeling or foreign body sensation, are brought about by compositions comprising at least, but not limited to, two semifluorinated alkanes. Semifluorinated alkanes are linear or branched alkanes some of whose hydrogen atoms have been replaced by fluorine. In a preferred embodiment, the semifluorinated alkanes (SFAs) used in the present invention are composed of at least one non-fluorinated hydrocarbon segment and at least one perfluorinated hydrocarbon segment. Particularly useful are SFAs which have one non-fluorinated hydrocarbon segment attached to one perfluorinated hydrocarbon segment, according to the general formula $F(CF_2)_n(CH_2)_mH$, or two perfluorinated hydrocarbon segments separated by one non-fluorinated hydrocarbon segment, according to the general formula $F(CF_2)_n(CH_2)_m(CF_2)_oF$.

Another nomenclature which is used herein refers to the above-mentioned SFAs having two or three segments as RFRH and RFRHRF, respectively, wherein $R_F$ designates a perfluorated hydrocarbon segment, $R_H$ designates a non-fluorinated segment. Alternatively, the compounds may be referred to as FnHm and FnHmFo, respectively, wherein F means a perfluorated hydrocarbon segment, H means a non-fluorinated segment, and n, m and o is the number of carbon atoms of the respective segment. For example, F3H3 is used for perfluoropropylpropane. Moreover, this type of nomenclature is usually used for compounds having linear segments. Therefore, unless otherwise indicated, it should be assumed that F3H3 means 1-perfluoropropylpropane, rather than 2-perfluoropropylpropane, 1-perfluoroisopropylpropane or 2-perfluoroisopropylpropane.

Preferably, the semifluorinated alkanes according to the general formulas $F(CF_2)_n(CH_2)_mH$ and $F(CF_2)_n(CH_2)_m(CF_2)_oF$ have segment sizes ranging from 3 to 20 carbon atoms, i.e. n, m and o are independently selected in the range from 3 to 20. SFAs which are useful in the context of the present invention are also described in EP-A 965 334, EP-A 965329 and EP-A 2110126, the disclosure of which documents is incorporated herein.

The compositions of the invention comprise at least, but not limited to, two semifluorinated alkanes. In particular, the SFA compositions in the present invention comprise of at least two semifluorinated alkanes of the formula $F(CF_2)_n(CH_2)_mH$. Preferably, at least two semifluorinated alkanes are miscible with one another. In a preferred embodiment, the composition comprise at least two semifluorinated alkanes of the formula $F(CF_2)_n(CH_2)_mH$, wherein one of the semifluorinated alkanes is a semifluorinated alkane of formula $F(CF_2)_n(CH_2)_mH$, wherein n is an integer from the range of 3 to 8 and m is an integer from the range of 3 to 10. In a further preferred embodiment, the composition comprises a first semifluorinated alkane of formula $F(CF_2)_n(CH_2)_mH$, wherein n is an integer from the range of 3 to 8 and m is an integer from the range of 3 to 10 and a second semifluorinated alkane of the formula $F(CF_2)_n(CH_2)_mH$ wherein n is an integer from the range of 6 to 20 and m is an integer from the range of 10 to 20. Most preferably, the first semifluorinated alkane is a liquid.

Without wishing to be bound by theory, it is assumed by the inventors that the first and the second semifluorinated alkanes differ in their effects on the eye and complement each other. As will be described in more detail below, the first semifluorinated alkane is typically a liquid compound which may act as a cleaning agent capable of solubilizing fatty materials which often obstruct the meibomian glands, whereas the second semifluorinated alkane is a solid compound which may act as lubricant for the cornea, thus substituting the lipid layer of the tear film, and function as a protective layer against evaporation of water.

In a further embodiment, the compositions of the present invention consist of at least two semifluorinated alkanes, wherein optionally one or more excipients may be included. As used herein, the terms "consist of", "consists of" and "consisting of" are so-called closed language meaning that only the mentioned components are present. In contrast, the expressions "comprise", "comprises" and "comprising" are used herein as so-called open language, meaning that further components may also be present. In a preferred embodiment, compositions consist of a first semifluorinated alkane of formula $F(CF_2)_n(CH_2)_mH$, wherein n is an integer from the range of 3 to 8 and m is an integer from the range of 3 to 10 and a second semifluorinated alkane of formula $F(CF_2)_n(CH_2)_mH$ wherein n is an integer from the range of 6 to 20 and m is an integer from the range of 10 to 20, and optionally one or more further excipients. In other words, the compositions according to this embodiment may comprise one or more further pharmacologically (substantially) inert additives, but no active ingredient. In this context, pharmacologically inert or substantially inert means that such excipient is considered, or commonly used, as inactive ingredient in pharmaceutical compositions.

Compositions free of active ingredient, or drug-free compositions, comprising at least two semifluorinated alkanes are also preferred. Particularly preferred are compositions free of, or excluding therapeutically effective amounts of active ingredient, comprising a first semifluorinated alkane of formula $F(CF_2)_n(CH_2)_mH$, wherein n is an integer from the range of 3 to 8 and m is an integer from the range of 3 to 10 and a second semifluorinated alkane of formula $F(CF_2)_n(CH_2)_mH$ wherein n is an integer from the range of 6 to 20 and m is an integer from the range of 10 to 20.

As used herein, active ingredient refers to any type of pharmaceutically active compound or derivative that is useful in the prevention, diagnosis, stabilization, treatment, or—generally speaking—management of a condition or disease.

Therapeutically effective amount refers to a dose, concentration or strength which is useful for producing a desired pharmacological effect. Such composition free of active ingredient does not act via a pharmacological mechanism, but is believed to act primarily through its physical effects at the site of administration.

Preferred SFAs of the formula $F(CF_2)_n(CH_2)_mH$, wherein n is an integer from the range of 3 to 8 and m is an integer from the range of 3 to 10 include, in particular, $F(CF_2)_4(CH_2)_5H$, $F(CF_2)_4(CH_2)_6H$, $F(CF_2)_6(CH_2)_4H$, $F(CF_2)_6(CH_2)_6H$, $F(CF_2)_6(CH_2)_8H$, and $F(CF_2)_6(CH_2)_{10}H$. Preferred SFAs of the formula $F(CF_2)_n(CH_2)_mH$, wherein n is an integer from the range of 6 to 20 and m is an integer from the range of 10 to 20 include, in particular, $F(CF_2)_8(CH_2)_{10}H$ and $F(CF_2)_{10}(CH_2)_{12}H$. Further preferred are compositions comprising at least one of $F(CF_2)_4(CH_2)_5H$, $F(CF_2)_4(CH_2)_6H$, $F(CF_2)_6(CH_2)_6H$, $F(CF_2)_6(CH_2)_3H$, and $F(CF_2)_6(CH_2)_{10}H$ and/or at least one of $F(CF_2)_3(CH_2)_{10}H$ and $F(CF_2)_{10}(CH_2)_{12}H$. In another embodiment, the composition comprises at least two SFAs selected from $F(CF_2)_4(CH_2)_5H$, $F(CF_2)_4(CH_2)_6H$, $F(CF_2)_6(CH_2)_4H$, $F(CF_2)_6(CH_2)_6H$, $F(CF_2)_6(CH_2)_3H$, and $F(CF_2)_6(CH_2)_{10}H$ and at least one of $F(CF_2)_3(CH_2)_{10}H$ and $F(CF_2)_{10}(CH_2)_{12}H$.

In a further embodiment, compositions may comprise at least two semifluorinated alkanes, wherein the weight ratio of the first semifluorinated alkane to the second semifluorinated alkane is at least about 3:1. Preferred are compositions comprising a first semifluorinated alkane of the formula $F(CF_2)_n(CH_2)_mH$, wherein n is an integer from the range of 3 to 8 and m is an integer from the range of 3 to 10, and a second semifluorinated alkane of the formula $F(CF_2)_n(CH_2)_mH$, wherein n is an integer from the range of 6 to 20 and m is an integer from the range of 10 to 20, wherein the weight ratio of the first semifluorinated alkane to the second semifluorinated alkane is at least about 3:1. Further preferred weight ratios of the first semifluorinated alkane to the second semifluorinated alkane are at least about 50:1 or at least about 30:1, or at least about 10:1.

Also preferred are compositions comprising at least two semifluorinated alkanes, wherein at least one semifluorinated alkane of formula $F(CF_2)_n(CH_2)_mH$ wherein n is an integer from the range of 6 to 20 and m is an integer from the range of 10 to 20 is dissolved or miscible in at least one semifluorinated alkane of formula $F(CF_2)_n(CH_2)_mH$, wherein n is an integer from the range of 3 to 8 and m is an integer from the range of 3 to 10.

In yet another embodiment, the compositions may comprise more than two semifluorinated alkanes. The compositions may comprise a third, fourth, etc. semifluorinated alkane. Preferably, compositions comprising a first semifluorinated alkane of formula $F(CF_2)_n(CH_2)_mH$, wherein n is an integer from the range of 3 to 8 and m is an integer from the range of 3 to 10 and a second semifluorinated alkane of formula $F(CF_2)_n(CH_2)_mH$ wherein n is an integer from the range of 6 to 20 and m is an integer from the range of 10 to 20, further comprise a semifluorinated alkane of the general formula $F(CF_2)_n(CH_2)_mH$ and/or the general formula $F(CF_2)_n(CH_2)_m(CF_2)_oF$. In a particular embodiment, compositions with a first and a second semifluorinated alkane further comprise a semifluorinated alkane of the formula $F(CF_2)_n(CH_2)_mH$, wherein n is an integer from the range of 4 to 15 and m is an integer from the range of 4 to 15.

Liquid SFAs are chemically and physiologically inert, colourless and stable. Their typical densities range from 1.1 to 1.7 g/cm$^3$, and their surface tension may be as low as 19 mN/m. SFAs of the $F(CF_2)_n(CH_2)_mH$ type are insoluble in water but also somewhat amphiphilic, with increasing lipophilicity correlating with an increasing size of the non-fluorinated segment.

Liquid SFAs of the RFRH type are being used commercially for unfolding and reapplying a retina, for long-term tamponade as vitreous humor substitute (H. Meinert et al., European Journal of Ophthalmology, Vol. 10(3), pp. 189-197, 2000), and as wash-out solutions for residual silicon oil after vitreo-retinal surgery. Experimentally, they have also been used as blood substitutes (H. Meinert et al., Biomaterials, Artificial Cells, and Immobilization Biotechnology, Vol. 21(5), pp. 583-95, 1993). These applications have established SFA's as physiologically well tolerated compounds.

The SFA compositions of the present invention are suited for ophthalmic compositions for topical administration. SFAs are well-tolerated by the eye, as shown in preclinical testing. In comparison, organic or non-aqueous solvents, perhaps with the exception of oily compounds, are typically very irritating or even highly damaging when administered topically to an eye.

Moreover, compared to oily carriers or vehicles in ophthalmic compositions for topical use, SFAs exhibit a refractive index which is much better compatible with the aim of a minimally affected vision: While oily preparation lead to a blurry vision and can therefore not be administered in any situation in which the patient needs a clear vision, SFAs cause little or no blurring.

By illustration, the refractive index of tear fluid is close to that of water, i.e. 1.333 at room temperature (RT). Oils typically have a substantially higher refractive index such as about 1.46 (peanut oil), 1.47 (sesame oil), or 1.48 (castor oil). In contrast, the inventors have determined the refractive indices of various SFAs of interest to be in the region of 1.29 to 1.35, i.e. much closer to that of water. In one of the specific embodiments, the invention is therefore practised with an SFA whose refractive index is from 1.29 to 1.35, and in particular from about 1.30 to about 1.35 at 20° C. The refractive index for selected SFAs is shown in table 1.

SFA compositions of the present invention are believed to have several functional effects when administered to the eye. Semifluorinated alkanes are able to mix and/or dissolve well with non-polar and lipophilic substances. It is proposed that SFAs of the formula $F(CF_2)_n(CH_2)_mH$, wherein n is an integer from the range of 3 to 8 and m is an integer from the range of 3 to 10 may be particularly useful for solubilizing meibum lipids and for removing abnormal and obstructive meibum found in clogged meibomian gland ducts.

TABLE 1

| SFA | Refractive index |
| --- | --- |
| F4H4 | 1.308 |
| F4H5 | 1.3204 |
| F4H6 | 1.334 |
| F4H7 | 1.3357 |
| F4H8 | 1.348 |
| F6H2 | 1.295 |
| F6H4 | 1.306 |
| F6H6 | 1.3224 |
| F6H7 | 1.3366 |
| F6H8 | 1.3432 |
| F6H9 | 1.3494 |

Meibum is the lipid secretion of the meibomian gland ducts and is normally secreted as a clear fluid comprising a complex mixture of polar and non-polar lipids such as cholesterol and wax esters, acyl glycerides, free fatty acids and phospholipids. In their dysfunctional state, the glands producing meibum may express secretions with an altered composition of those lipids which exhibit increased viscosity and which may also contain particulate cellular material. Such secretions can obstruct the gland ducts and may be ineffective for forming a functional stable and continuous tear film lipid layer, leading to lipid tear film deficiency, and the condition and symptoms of keratoconjunctivitis sicca. It is proposed that semifluorinated alkane compositions comprising at least two SFAs, one of which is an SFA of the formula $F(CF_2)_n(CH_2)_mH$, wherein n is an integer from the range of 3 to 8 and m is an integer from the range of 3 to 10 may be effective in solubilizing, in particular, obstructing and/or viscous meibomian secretions comprising polar and non-polar lipids such as cholesterol and wax esters, acyl glycerides, free fatty acids and phospholipids, thus enhancing their clearance from the eye.

In addition, it is further proposed that the SFA compositions of the present invention can also serve as either a replacement, substitute or supplement to the tear film lipid layer. For patients suffering from dry eye syndrome, the SFA compositions of the present invention may have a lubricating as well as a protective effect. It is believed that the SFA compositions are capable of forming a protective film over the corneal surface and prevent aqueous evaporative loss of the tear film. In particular, SFAs of formula $F(CF_2)_n(CH_2)_mH$ wherein n is an integer from the range of 6 to 20 and m is an integer from the range of 10 to 20 are thought to be useful in this capacity, such as by mixing with, and supplementing the existing tear film lipid layer, or forming a film over the corneal surface. Evaporation of the tear film generally leads to tear hyperosmolarity, which can lead to the triggering of undesirable inflammatory pathways. SFAs, being non-aqueous, have no osmolarity. Consequently, unlike some conventional aqueous ophthalmic preparations (which have intrinsic, and often high, osmolarity), SFA compositions will not contribute to tear hyperosmolarity and have, in fact, an opposing and protective effect through the prevention of tear evaporation.

Furthermore, due to the similarity of their refractive indexes with water, SFAs are particularly suited to the purpose of replacing, supplementing, or mixing with the tear film, compared to lipid substitutes such as castor oil or mineral oil which have been used in prior art eye formulations and which can confer a haze or blurriness to the vision upon and also for significant periods of time after instillation. SFAs also have improved lubricating properties which help minimize stinging or grainy sensations often experienced by the patient upon application of aqueous-based compositions.

Compositions comprising at least a first semifluorinated alkane of the formula $F(CF_2)_n(CH_2)_mH$, wherein n is an integer from the range of 3 to 8 and m is an integer from the range of 3 to 10, and at least a second semifluorinated alkane of the formula $F(CF_2)_n(CH_2)_mH$, wherein n is an integer from the range of 6 to 20 and m is an integer from the range of 10 to 20 are believed to have the dual function of solubilizing or aiding in the removal of obstructive or viscous meibum lipids and serving as a tear film lipid layer replacement, as described above. As such, these compositions are particularly useful in the treatment of meibomian gland dysfunction and/or keratoconjunctivitis sicca and conditions and symptoms associated therewith.

Moreover, SFAs exhibit a remarkable wetting and spreading behaviour by which they can rapidly and effectively spread over the corneal surface and conjunctiva. Wetting means the ability of a liquid to establish and maintain contact with a solid surface, resulting from intermolecular interactions when the two are brought together. The balance between adhesive and cohesive forces determines the degree of wetting. The higher the adhesive forces compared to the cohesive forces, the more a drop of liquid will spread across the surface of the solid material. Conversely, very high cohesive forces within the liquid will cause the drop to form a sphere, thus avoiding contact with the surface. Similarly, spreading may also occur at the interface of two liquids which are brought into contact with each other.

A measure for wetting and spreading is the contact angle θ. The contact angle is the angle at which the liquid-vapour interface meets the solid-liquid or liquid-liquid interface. The tendency of a drop to spread out increases as the contact angle decreases. Thus, the contact angle provides an inverse measure of wettability.

A low contact angle of less than 90° indicates high wettability and/or spreading, whereas a higher contact angle indicates poor wettability and spreading. Perfect wetting and spreading results in a contact angle of 0°, also reported as no measurable contact angle.

SFAs exhibit excellent wetting of various surfaces. For example, the contact angle of both F4H5 and F6H8 on tablets compressed from either trospium chloride or fenofibrate (150 mg of drug substance compressed at 15-20 kN to tablets of 13 mm in diameter) is not measurable, i.e. there is perfect wetting. It is noted that fenofibrate is an example of a hydrophobic, poorly water-soluble compound, whereas trospium chloride is hydrophilic and water-soluble. For comparison, the contact angle of purified water on the fenofibrate tablet was determined as 92.5°, i.e. the tablet was poorly wetted by water.

It has now been found by the inventors that compositions comprising at least two SFAs as defined herein can exhibit surprisingly enhanced spreading behaviour compared to SFAs alone or SFAs in combination with non-fluorinated or fluorinated organic solvents. For example, when a 50-4 droplet of a solution of $F(CF_2)_{10}(CH_2)_{12}H$ in $F(CF_2)_4(CH_2)_5H$ was administered to a glass surface, an almost two-fold increase in the spread area of the droplet, compared to $F(CF_2)_4(CH_2)_5H$ alone, was observed (Table 2).

TABLE 2

| Liquid droplet surface area (2 minutes after application of 50 μL of liquid to a glass surface) | |
|---|---|
| Substance | Liquid covered surface area [cm$^2$] |
| F4H5 | 7.54 ± 0.33 |
| F4H5/F10H12 (27 mg/mL) | 14.12 ± 0.57 |
| F4H5/F10H10 (27 mg/mL) | 12.28 ± 0.16 |
| F4H5/F8H10OH (27 mg/mL) | 1.43 ± 0.31 |
| F6H8 | 12.89 ± 0.94 |
| F6H8/F10H12 (27 mg/mL) | 14.28 ± 0.29 |
| F6H8/F10H10 (27 mg/mL) | 13.21 ± 0.73 |
| F6H8/F8H10OH (27 mg/mL) | 1.62 ± 0.39 |
| Nonane | 5.20 ± 0.18 |
| Nonane/F10H12 (27 mg/mL) | 1.96 ± 0.07 |
| Perfluorodecalin | 1.45 ± 0.02 |

Figure 1:
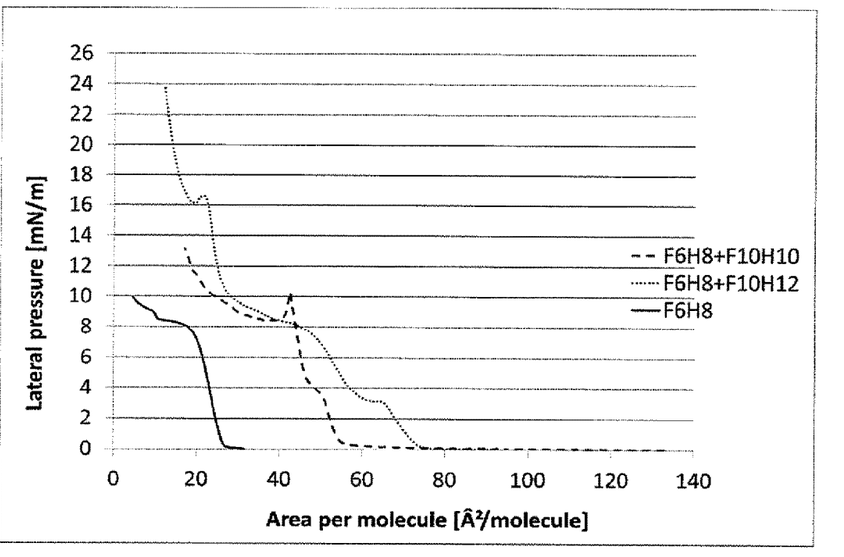

Monolayer films formed by compositions comprising at least a first semifluorinated alkane of the formula $F(CF_2)_n(CH_2)_mH$, wherein n is an integer from the range of 3 to 8 and m is an integer from the range of 3 to 10, and at least a second semifluorinated alkane of the formula $F(CF_2)_n(CH_2)_mH$, wherein n is an integer from the range of 6 to 20 and m is an integer from the range of 10 to 20 have moreover increased stability than compared to those formed by a single SFA alone. Langmuir isotherm experiments of neat F6H8 ($F(CF_2)_6(CH_2)_8H$), for example, demonstrate that it does not form a stable monolayer. In contrast, it has been found that isotherms of a mixture of F6H8 with a semifluorinated alkane of the formula $F(CF_2)_n(CH_2)_mH$, wherein n is an integer from the range of 6 to 20 and m is an integer from the range of 10 to 20 (i.e. F10H12 and F10H10) demonstrate stable film monolayer characteristics (FIG. 1).

The enhanced spreading behaviour and stable film properties of such combinations of SFAs are particularly advantageous for ophthalmic compositions in general and for ophthalmic compositions aimed at treating the dry eye condition. A droplet administered to the surface of the eye may lead to rapid spreading of the SFA mixture compositions over the corneal surface and the formation of a film. Efficient spreading would allow for a more effective distribution over the ocular surface. A stable film that does not immediately break up would also provide a longer-lasting lubricating effect on the ocular surface.

Overall, there would be significantly less reliance placed on the blinking mechanism of the patient (which may be ineffective or hindered by the diseased state) to spread the composition over the ocular surface. It is believed that the compositions of the invention may thus be more efficiently administered to the ocular surface, in comparison with conventional formulations which are generally aqueous based and have poorer spreading behaviour. As such, less frequent administration to the dry eye for relief may be achieved with these compositions.

A further advantage of the invention that is based on the use of more than one SFA is that they can be designed or mixed for optimally adjusted residence time after administration, i.e. the viscosity and evaporation behaviour of the composition can be tuned. This provides an additional means in which to optimize the formulation of an ophthalmic composition for a more effective residence time in the eye.

In addition, SFAs are also capable of forming very small droplets when dispensed from a dropper such as an eye dropper. Without wishing to be bound by theory, it is believed that the small droplet size is a result of an interplay of the SFA's unique properties in terms of their density, viscosity, and surface tension. In any case, it is believed that for topical administration into an eye a small drop or volume of administration is highly advantageous as the capability of the lacrimal sac to accept and hold fluid is extremely limited. In fact, it is very common that the administration of a conventional eye drop formulation based on water or oil immediately leads to a discharge of a substantial fraction of the administered medicine as well as some tear fluid. At the same time, there is a risk that some of the administered dose will be taken up systemically via the nasolacrimal duct.

The invention also provides a means of formulating non-aqueous ophthalmic compositions which are microbiologically stable. Aqueous ophthalmic compositions are prone to bacterial contamination. In comparison, SFAs have bacteriostatic properties and do not support microbial growth. Hence, it is possible to formulate preservative-free ophthalmic compositions which are better tolerable for many patients, in particular patients suffering from keratoconjunctivitis sicca. Such compositions also do not promote bacterial infection of the eye lid margin in patients who, for example, are suffering from obstructed or blocked meibomian glands.

The compositions of the invention are thus very well suited for the topical administration to an eye or ophthalmic tissue. Ophthalmic tissue includes any surface of the eye anatomy that is, or can be (i.e. by non-surgical means) topically exposed. Preferably, the compositions are administered to the cornea or conjunctiva. The compositions are also preferably administered to the upper or lower eye lid margins, meibomian gland ducts, eyelashes or any area of the eye or eye lid anatomy.

In a further embodiment, the compositions of the invention can be used for the palliative treatment and care of the eye or ophthalmic tissue. The compositions can be used as a palliative measure, i.e. to alleviate or relieve ocular symptoms associated ophthalmic disorders or conditions, including keratoconjunctivitis sicca and meibomian gland dysfunction. For example, they may be used in addition to medicines comprising an active ingredient whose dosing frequency is typically limited by tolerability or safety concerns. The compositions may also be used as a palliative measure for alleviating or relieving any non-disease related sensation of dryness, irritation, or discomfort of the eye. Preferably, compositions consisting of at least two or more semifluorinated alkanes and optionally one or more further excipients are used in the palliative treatment and care of any eye or ophthalmic tissue. The said compositions are administered not to cure, prevent or intervene in any of the root etiological pathways of an ophthalmic disease and its symptoms, but may be applied for the sole purpose of alleviating and relieving the symptoms of said disease. Particularly preferred is the use of the compositions of the invention as artificial tears, tear substitutes or tear replacements or eye lubricants. Said compositions may be used concomitantly or in conjunction with eye compositions with pharmaceutically active ingredients (e.g. immunosuppressant eye drops) that are aimed at curing or treating the root causative pathways of an ophthalmic disease. In the use of the said compositions for the palliative treatment and care of the eye or ophthalmic tissue, the compositions may be administered one or more times daily.

In yet another further embodiment, the compositions of the invention may be used as a cleansing solution for the eye or ophthalmic tissue. The compositions are preferably used to cleanse or help remove or wash away any accumulated debris or discharge such as meibum secretions from the eye lid, eye lid margins, eye lashes, or eye crevices. Compared to aqueous formulations, the SFA compositions are able to spread more readily, and thus are able to reach the more difficult to access regions of eye lid anatomy. In a particular embodiment, the compositions for use as a cleansing solution are formulated to be administered as a spray. This can be useful for patients either averse to, or unable to apply the compositions via eye drops.

Optionally, the compositions of the invention may further comprise lipophilic vitamin derivatives. It is noted that vitamins and vitamin derivatives, depending on the exact compound and strength, may also be considered as active ingredients. Lipophilic vitamin derivatives include vitamin A and their derivatives, for example, retinol and its esters (e.g. retinol palmitate or retinol acetate), retinoic acid, retinal, as well as other retinoid derivatives and their esters; vitamin E (e.g. α-tocopherol) and their derivatives (e.g. tocotrienols) and esters (e.g. tocopherol acetate or tocopherol TPGS). In an embodiment of the invention, liquid compositions comprising at least two or more semifluorinated alkanes further comprise at least one solubilized lipophilic vitamin or vitamin derivative.

In yet another embodiment, the compositions of the invention may further comprise polyunsaturated fatty acids such as omega-3 fatty acids and/or omega-6 fatty acids. Such fatty acids may contribute to the tear film lipid layer and may be native to the tear film lipid layer. Omega-3 fatty acids can have an anti-inflammatory effect. They serve as precursors for the biosynthesis of anti-inflammatory mediators such as resolvins and protectins. It is noted, that such fatty acids and their derivatives, depending on the exact concentration and strength, may be considered as active ingredients. Examples of omega-3 fatty acids (also known as ω-3 fatty acids or n-3 fatty acids) include eicosapentaenoic acid (EPA), docosahexaenoic acid (DHA), alpha-linolenic acid (ALA). Examples of omega-6 fatty acids (also known as ω-6 fatty acids or n-6 fatty acids) include gamma-linolenic acid, linoleic acid, dihomo-gamma-linolenic acid. Derivatives of omega-3 fatty acids or omega-6 fatty acids, such as alkyl ester derivatives are also within the scope of the invention. Particularly preferred alkyl ester derivatives are eicosapentaenoic acid ethyl ester or docasahexaenoic acid ethyl ester. Derivatives of eicosapentaenoic acid or docosahexaenoic acid such as resolvins and neuroprotectins are also considered. In a particular embodiment, liquid compositions comprising at least two or more semifluorinated alkanes further comprise one or more omega-3-fatty acid or omega-3-fatty acid derivative, and/or omega-6 fatty acid or omega-6 fatty acid derivative.

The compositions of the invention may also optionally further comprise carotenoid and carotenoid derivatives, in particular xanthophylls. Particularly preferred are lutein and zeaxanthin. Derivatives of lutein or zeaxanthin, such as lutein or zexathin esters are also considered. In a particular embodiment, liquid compositions comprising at least two or more semifluorinated alkanes further comprise lutein or a derivative thereof.

In another embodiment, the compositions of the invention may also further comprise flavan-3-ols such as catechins. Catechin or catechin isomers (e.g. epicatechin) and derivatives (for example, ester derivatives of catechin) are particularly preferred.

Optionally, one or more further excipients may be used in the SFA compositions. Additional excipients may also, in addition to the SFAs serve to contribute to the deficient tear film and tear film lipid layer in patients with keratoconjunctivitis sicca, related conditions, and symptoms associated therewith. Preferred are excipients that are biocompatible and are tolerated by the eye, and which are liquid and/or soluble and miscible in SFAs. In particular, excipients are preferably selected from lipids, oils, lipophilic vitamins, lubricants, viscosity agents, antioxidants surfactants and mixtures of two or more thereof.

Examples of potentially useful lipids and oily excipients and which may be included in the SFA compositions of the invention include triglyceride oils (e.g. soybean oil, olive oil, sesame oil, cotton seed oil, castor oil, sweet almond oil), mineral oil (e.g. petrolatum and liquid paraffin), medium chain triglycerides (MCT), oily fatty acids, isopropyl myristate, oily fatty alcohols, esters of sorbitol and fatty acids, oily sucrose esters, oily cholesterol esters, oily wax esters, glycerophospholipids, sphingolipids, or any oily substance which is physiologically tolerated by the eye. Any synthetic, semi-synthetic or natural oily excipients which mimic or are structurally analogous or related to the components naturally found in the tear film lipid layer are also within the scope of the invention.

Examples of potentially useful lipophilic vitamin excipients include vitamin A and their derivatives, for example, retinol and its esters (e.g. retinol palmitate or retinol acetate), retinoic acid, retinal, as well as other retinoid derivatives and their esters; vitamin E (e.g. α-tocopherol) and their derivatives (e.g. tocotrienols) and esters (e.g. tocopherol acetate or tocopherol TPGS). In an embodiment of the invention, liquid compositions comprising at least two or more semifluorinated alkanes further comprise at least one lipophilic vitamin excipient that is completely solubilized. Further preferred are compositions consisting of at least two or more semifluorinated alkanes and one or more further excipients, wherein at least one of the excipients is a lipophilic vitamin.

Examples of potentially useful fatty acid excipients include polyunsaturated fatty acids such as omega-3 fatty acids and/or omega-6 fatty acids. Such excipients may contribute to the tear film lipid layer and may be native to the tear film lipid layer. Examples of omega-3 fatty acid (also known as ω-3 fatty acids or n-3 fatty acids) excipients include eicosapentaenoic acid (EPA), docosahexaenoic acid (DHA), alpha-linolenic acid (ALA). Examples of omega-6 fatty acid (also known as ω-6 fatty acids or n-6 fatty acids) excipients include gamma-linolenic acid, linoleic acid, dihomo-gamma-linolenic acid. Derivatives of omega-3 fatty acids or omega-6 fatty acids, such as alkyl ester derivatives, are also within the scope of the invention as excipients. Particularly preferred alkyl ester derivatives are eicosapentaenoic acid ethyl ester or docasahexaenoic acid ethyl ester.

In a particular embodiment, liquid compositions comprising at least two or more semifluorinated alkanes further comprise one or more omega-3-fatty acid excipients or omega-6 fatty acid excipient. Further preferred are compositions consisting of at least two or more semifluorinated alkanes and one or more further excipients, wherein at least one of the excipients is an omega-3 fatty acid excipient or an omega-6 fatty acid excipient, or derivatives thereof.

Examples of potentially useful lubricants and/or viscosity agents include carboxymethyl cellulose, hydroxymethyl cellulose, hydroxypropyl cellulose, glycerol, polyvinyl alcohol, polyethylene glycol, propylene glycol, hyaluronic acid, hydroxypropyl guar.

Examples of potentially useful antioxidant excipients include carotenoid and carotenoid derivatives, in particular xanthophylls. Particularly preferred are lutein and zeaxanthin. Derivatives of lutein or zeaxanthin, such as lutein or zexathin esters are also considered. Other preferred antioxidant excipients considered to be potentially useful include flavan-3-ols such as catechins. Catechin or catechin isomers (e.g. epicatechin) and their derivatives (for example, ester derivatives of catechin) are particularly preferred.

Potentially useful surfactant excipients include in particular non-ionic surfactants or amphiphilic lipids. Surfactants which are considered potentially useful include tyloxapol, poloxamers such as Pluronic F68LF or Lutrol F68, Pluronic L-G2LF and Pluronic L62D, polysorbates such as polysorbate 20 and polysorbate 80, polyoxyethylene castor oil derivatives, sorbitan esters, polyoxyl stearates, and mixtures of two or more thereof.

The composition may of course comprise further excipients as required or useful such as acids, bases, electrolytes, buffers, solutes, antioxidants, stabilisers, synergists, and—if required in a particular case—a preservative. The compositions may be formulated to be administered as a liquid solution, gel, emulsion, microemulsion, suspension, or spray. They may be prepared by commonly known techniques for the manufacture of said liquid solutions, gels, emulsions, microemulsion, suspensions, or sprays.

Furthermore, the invention provides a pharmaceutical kit comprising the composition as described above and a container holding the composition. Preferably, the container which contains the composition has a dispensing means such as a dropping device adapted for topically administering the composition to the eye of a patient.

EXAMPLE

Example 1

Langmuir-Blodgett isotherm measurements were taken for neat F6H8 (F(CF$_2$)$_6$(CH$_2$)$_3$H), and for mixtures of F$_6$H$_8$ with F$_{10}$H$_{10}$ (F(CF$_2$)$_{10}$(CH$_2$)$_{10}$H) and with F$_{10}$H$_{12}$ ((F(CF$_2$)$_{10}$(CH$_2$)$_{12}$H).

A solution of F6H8 in chloroform (1 mg/mL) was prepared. 594 of this solution was spread onto a Langmuir-Blodgett trough with Milli-Q-purified water as the sub-phase at 25° C. After allowing the solvent to evaporate (15 min), compression was initiated at a barrier rate of 4 cm²/min. Similar conditions were used for the semifluorinated alkane mixtures.

In result, the isotherm of neat F6H8 ($F(CF_2)_6(CH_2)_3H$) demonstrated that it has poor capability for forming a stable monolayer. The isotherm shows predominantly a liquid expanded (LE) characteristics, upon further compression there appears to be only a very brief ordered liquid condensed (LC) phase. The isotherms of the mixtures of F6H8/F10H10 and F6H8/F10H12 in contrast show a significantly detectable transition of an LE phase to the more ordered LC phase, and monolayer collapse occurs only at higher pressure values (FIG. 1).

The invention claimed is:

1. A method for solubilizing meibum and removing abnormal and obstructive meibum from obstructed meibomian gland ducts in a patient in need thereof, comprising topically administering a liquid semifluorinated alkane to the cornea or conjunctiva of the eye of the patient, wherein the semifluorinated alkane spreads over the corneal surface or conjunctiva; and
  wherein said semifluorinated alkane is $F(CF_2)_6(CH_2)_8H$ (F6H8), and wherein said semifluorinated alkane is administered in the absence of any therapeutically effective amount of a pharmaceutically active drug substance useful for the topical ophthalmic treatment of keratoconjunctivitis sicca; and
  wherein the patient has keratoconjunctivitis sicca which is caused by meibomian gland dysfunction.

2. The method according to claim 1, wherein the patient has dysfunctional meibomian gland ducts.

3. The method according to claim 2, wherein the patient has lipid tear film deficiency, and the condition and symptoms of keratoconjunctivitis sicca.

4. The method according to claim 1, wherein the semifluorinated alkane is administered in the absence of water and in the absence of a preservative.

5. The method according to claim 1, wherein said patient also receives treatment concomitantly or in conjunction with one or more additional eye compositions comprising pharmaceutically active ingredients.

6. A method of treating keratoconjunctivitis sicca which is caused by meibomian gland dysfunction comprising topically administering a liquid semifluorinated alkane to the cornea or conjunctiva of an eye of a patient in need thereof, wherein the semifluorinated alkane is administered in the absence of water and in the absence of a preservative, wherein the semifluorinated alkane is $F(CF_2)_6(CH_2)_8H$ (F6H8), and wherein the semifluorinated alkane spreads over the corneal surface or conjunctiva;
  and wherein said semifluorinated alkane is administered in the absence of any therapeutically effective amount of a pharmaceutically active drug substance useful for the topical ophthalmic treatment of keratoconjunctivitis sicca, and wherein the patient has keratoconjunctivitis sicca which is caused by meibomian gland dysfunction.

7. The method according to claim 6, wherein the semifluorinated alkane is administered to the cornea or conjunctiva of an eye of the patient in an amount effective to solubilize meibum and remove abnormal and obstructive meibum from obstructed meibomian gland ducts.

8. The method according to claim 7, wherein the semifluorinated alkane is also administered to the upper or lower eye lid margins, meibomian gland ducts eyelashes or any area of the eye lid anatomy.

9. The method according to claim 6, wherein said patient also receives treatment concomitantly or in conjunction with one or more additional eye compositions comprising pharmaceutically active ingredients.

10. The method according to claim 1, wherein the method comprises topically administering a composition which consists of the F6H8.

11. The method according to claim 6, wherein the method comprises topically administering a composition which consists of the F6H8.

* * * * *